United States Patent
Elliott et al.

(10) Patent No.: US 11,488,725 B2
(45) Date of Patent: Nov. 1, 2022

(54) AUTOMATED INTRAOCULAR LENS SELECTION PROCESS

(71) Applicants: Carl Zeiss Meditec, Inc., Dublin, CA (US); Carl Zeiss Meditec AG, Jena (DE)

(72) Inventors: Jeremiah Robert Elliott, Temple, TX (US); Kyle Hunter Smith, Temple, TX (US)

(73) Assignees: CARL ZEISS MEDITEC, INC., Dublin, CA (US); CARL ZEISS MEDITEC AG, Jena (DE)

(*) Notice: Subject to any disclaimer, the term of this patent is extended or adjusted under 35 U.S.C. 154(b) by 0 days.

(21) Appl. No.: 16/762,267

(22) PCT Filed: Nov. 9, 2018

(86) PCT No.: PCT/EP2018/080718
§ 371 (c)(1),
(2) Date: May 7, 2020

(87) PCT Pub. No.: WO2019/092165
PCT Pub. Date: May 16, 2019

(65) Prior Publication Data
US 2020/0350080 A1 Nov. 5, 2020

Related U.S. Application Data

(60) Provisional application No. 62/583,968, filed on Nov. 9, 2017.

(51) Int. Cl.
*G16H 70/20* (2018.01)
*G16H 20/40* (2018.01)

(52) U.S. Cl.
CPC ............ *G16H 70/20* (2018.01); *G16H 20/40* (2018.01)

(58) Field of Classification Search
CPC .... G16H 70/20; G16H 20/40; A61F 9/00736; A61F 9/00781; A61F 9/00804;
(Continued)

(56) References Cited

U.S. PATENT DOCUMENTS

| | | | |
|---|---|---|---|
| 6,801,913 B2 | 10/2004 | Matsumura et al. | |
| 2017/0027437 A1 | 2/2017 | Neal et al. | |

FOREIGN PATENT DOCUMENTS

| | | |
|---|---|---|
| EP | 2983619 B1 | 5/2018 |
| WO | 2009/076670 A1 | 6/2009 |

(Continued)

OTHER PUBLICATIONS

Ewbank, Alison ; Trends in laser refractive surgery in the UK 2005; The Optician 230.6029: 14-18,20. Mark Allen Group Ltd. (Nov. 25, 2005) (Year: 2005).*

(Continued)

*Primary Examiner* — Hiep V Nguyen
(74) *Attorney, Agent, or Firm* — Morrison & Foerster LLP

(57) ABSTRACT

A surgery planning system obtains data from a doctor's questionnaire, patients questionnaire, EMR, and biometry unit. The data is weight-mapped to a plurality of electives in a plurality of options (categories). A surgery plan is generated based on the weights of the patients answers, EMR data, and biometry unit data.

19 Claims, 12 Drawing Sheets

(58) Field of Classification Search
CPC .............. A61F 9/00812; A61F 9/00827; A61F 9/00829; A61B 3/0025; A61B 3/1015; A61B 3/103; A61B 2034/102; A61B 34/10; A61B 3/0091; A61B 3/1005; A61B 3/102; A61B 3/107; A61B 3/112; A61B 3/117; A61B 3/1173; A61B 3/18
USPC .......................................................... 705/2
See application file for complete search history.

(56) References Cited

FOREIGN PATENT DOCUMENTS

| WO | WO-2009076670 A1 * | 6/2009 | ........... A61F 2/1618 |
|----|----|----|----|
| WO | 2012/050622 A2 | 4/2012 | |
| WO | WO-2012050622 A2 * | 4/2012 | ............... A61B 3/14 |
| WO | WO-2012150279 A1 * | 11/2012 | ........... A61B 3/0025 |

OTHER PUBLICATIONS

International Search Report and Written Opinion received for PCT Patent Application No. PCT/EP2018/080718, dated Feb. 20, 2019, 14 pages.
International Preliminary Reporton Patentability received for PCT Patent Application No. PCT/EP2018/080718, dated May 22, 2020, 10 pages.

* cited by examiner

Caroline  80 years old / Female

Data Confidence
Confidence bar

Cataract extraction with IOL
Right eye
Surgeon: Tom Crow

| Doctor Driven | Patient Driven |

Patient Questionnaire

1. Distance vision complaint? — Yes
2. Glare complaint? — Yes
3. Glare complaint? — Yes
4. Near vision complaint? — No
5. Profession? — Driver
6. Drive after dark? — Yes
7. History of monovision? — Never tried
8. Less dependent on glasses? — Yes
9. Prefer distance or distance an… — Dist & Near Clear Answers Q & A    Plan

AUTOMATED INTRAOCULAR LENS SELECTION PROCESS

PRIORITY

This application is a National Phase application under 35 U.S.C. § 371 of International Application No. PCT/EP2018/080718, filed Nov. 9, 2018, which claims priority to U.S. Provisional Application Ser. No. 62/583,968, filed Nov. 9, 2017, the contents of which are hereby incorporated by reference in their entirety.

The present invention is generally directed to the field of medical equipment. More specifically, it is directed to medical tools for surgery planning, and in particular eye-related surgery.

Surgical planning is a preoperative method of pre-visualizing a surgical intervention (including surgical procedures, incision description, etc.), in order to predefine surgical steps. The transfer of the surgical planning to the patient is generally made using a medical navigation system, which may include various computer-assisted surgical equipment.

Planning for cataract surgery can be complicated because of the many options and possible complications. Typically, a surgeon reviews patent diagnostic data and relies on prior experience to take a heuristic approach toward cataract surgery planning. Since each surgeon has different preferences, such as regarding lens types, lens manufactures, and surgical procedures, this approach may be a bit of an art.

Cataract surgery involves the use of an intraocular lens (IOL), but there are many different IOL types and manufacturers. Different calculations (formulations) are needed for the different IOL types in order to optimize the probability of obtaining a desired refraction after surgery. These calculations are provided by different "calculators" (IOL power estimation formulas and toric calculators) that use different criteria and algorithms to arrive at their solutions. Some of these calculators may only be available on the internet (online) from a specific provider. Gaining access to these different calculators may be problematic.

Prior art approaches toward alleviating these problems have been put forth. For example, the Verion Reference Unit (part of the Verion System from Alcon Corp.) is an eye-diagnostic testing device that captures various diagnostic measurements and eye images. It also includes planning software to assist a surgeon in developing a surgery plan. Captured measurement data is imported into the planning software to prepopulate various data fields. If a surgeon already knows a desired post-operative (post-op) refraction target and already which IOL models, or types, to consider, then the Verion Reference Unit provides a pull-down menu with a selection of some established formulas (e.g., Holladay II, Haigis, Holladay I, Hoffer-Q, and SRK-T). If a calculator in the pull-down menu is suitable for an IOL model, the surgeon may use it to help select an appropriate IOL and lens power for a patient. Because the Verion Reference Unit is a stand-alone, physical, eye-diagnostic testing device, it is limited to treating the eye as an isolated optical system and cannot provide any assistance beyond its specific diagnostic measurements.

It is an object of the present invention to provide a method/device/system for assisting in the generating of an eye surgery plan, for example a cataract surgery plan.

It is a further object of the present invention to provide a method/device/system that provides a post-op refraction target recommendation, IOL type recommendation, and IOL model recommendation with minimal doctor input.

The above objects are met in a system and method for generating a surgical plan that combines inputs from multiple sources and provides a web-based interface.

A method and system for generating an eye (cataract) surgery plan for a patient may include electronically/digitally interfacing with a diagnostic data store or biometry unit to obtain diagnostic data indicative of physical attributes of the patient's eye, and predefined as corresponding to a group of options related to cataract surgery planning. That is, obtained diagnostic data is mapped to one or more surgery planning options (e.g., options that provides a surgery planning component, or recommendation) because its information has been determined to be useful in scoring a particular surgery-related recombination choice, or elective. Each option within the group of options has a plurality of electives, and select individual diagnostic datum, among the obtained diagnostic data, has a set of diagnostic-datum weights that corresponds to electives within the groups of options. For example, the group of options (or categories) may include a target refractive condition category for a patient, an intraocular lens (IOL) type category, a surgical procedure category, and a surgery eligibility category. Each option, or category, within the group of options may have multiple electives. For example, the electives for the target refractive condition category may include "near", "intermediate", and "far". These "targets" are generally standardized in the field and need not be defined here. The elective for the surgical procedure category may include Limbal Relaxing Incisions (LRI), Femtosecond laser-assisted cataract surgery (FLAGS), and Post-op laser-assisted in situ keratomileusis (LASIK). The electives for the IOL type category may include monofocal IOL, Toric IOL, multifocal IOL, EDOF IOL, etc. Electives for the eligibility option may include conditions that may be needed to determine eligibility for cataract surgery, such as "Distance Vision impaired", "Near Vision Impaired", and "Impaired by Glare". Obtained medical history datum may have a set of medical-datum weights corresponding to electives (or elections) within the group of options.

Additionally, an electronic patient questionnaire is used to obtain patient answers that are associated with a set of patient-datum weights that correspond to electives within the group of options. The system may then generate at least one of a post-operative refractive-target candidate (e.g., near, intermediate, or far) that best fits the patient's expectations and an intraocular lens-type candidate based at least in part on the diagnostic-datum weights and the patient-datum weights.

The present system may further electronically/digitally interface with an electronic medical record (EMR) system, e.g., over the internet or over a local area network, to extract (obtain) medical history data (EMR data). The selected EMR data may be predefined as corresponding to the group of options (or categories) related to cataract surgery planning. In generating at least one of the post-operative refractive-target candidate and the intraocular lens-type candidate, at least one elective may be eliminated from consideration based on the obtained EMR data.

Other objects and attainments together with a fuller understanding of the invention will become apparent and appreciated by referring to the following description and claims taken in conjunction with the accompanying drawings.

The embodiments disclosed herein are only examples, and the scope of this disclosure is not limited to them. Embodiments according to the invention are disclosed in the attached claims directed to a method, a storage medium, a system, a device and/or a computer program product, wherein any feature mentioned in one claim category, e.g. method, can be claimed in another claim category, e.g. system, as well. The dependencies or references back in the attached claims are chosen for formal reasons only. However, any subject matter resulting from a deliberate reference back to any previous claims can be claimed as well, so that any combination of claims and the features thereof are disclosed and can be claimed regardless of the dependencies chosen in the attached claims.

In the drawings wherein like reference symbols refer to like parts:

FIG. 1A: illustrates an overview of a surgical planning system in accord with the present invention.

FIG. 1B: illustrate an overview of an alternate embodiment wherein the surgical planning system of FIG. 1A is implemented as a cloud-based system.

FIG. 2: illustrates an approach to accessing multiple different EMRs, such as via the Internet.

FIG. 3: illustrates a data structure to score surgical plan options relative to patient answers.

FIG. 4: illustrates an example embodiment of a digital device and system.

FIG. 5: illustrates an example of clinical questions posed to a doctor or clinician.

FIG. 6: illustrates an example summary of patient questions.

Figure 7:
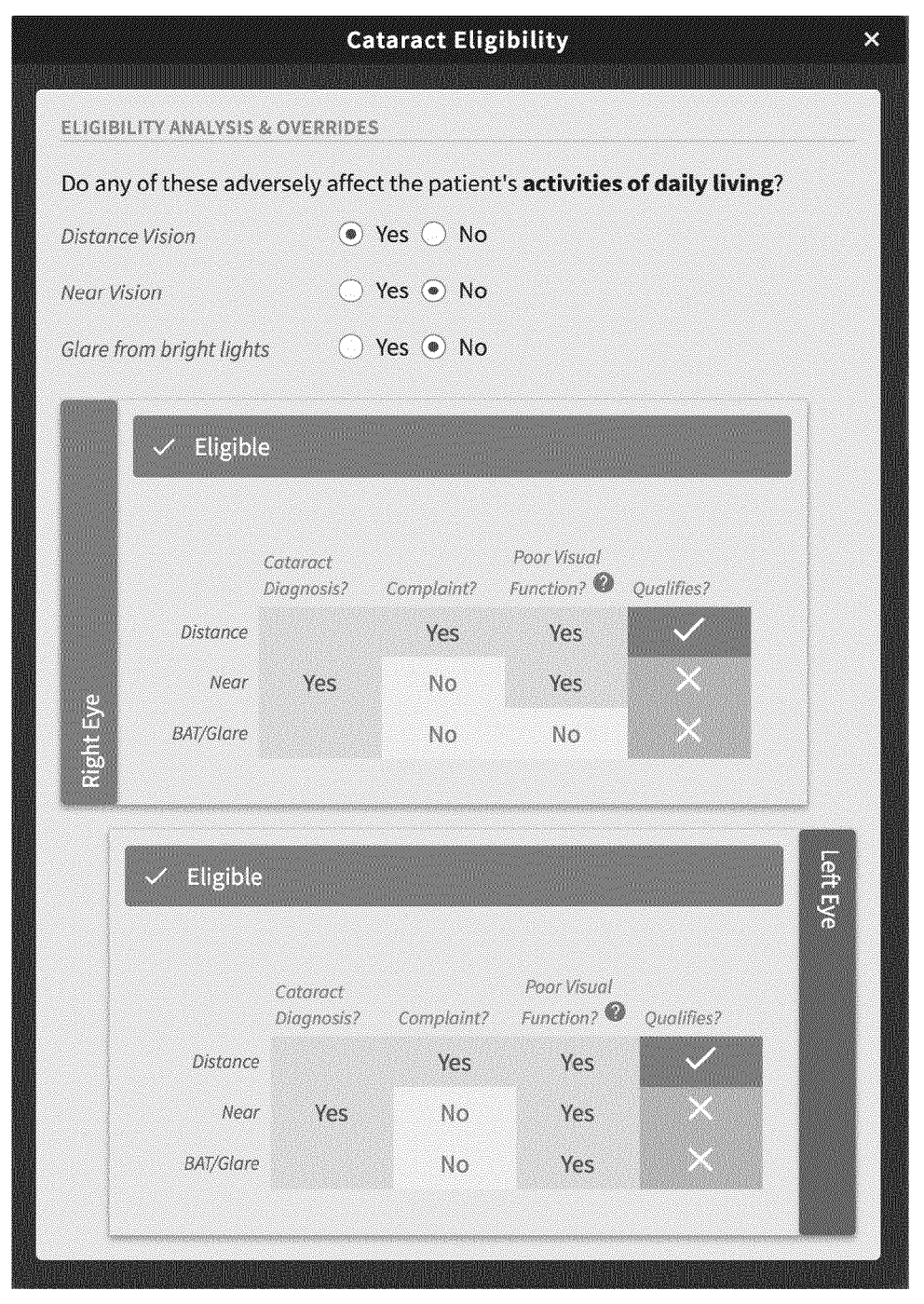

FIG. 7: illustrates an example interface to determine eligibility for cataract surgery.

FIG. 8: illustrates an example interface displaying alerts.

FIG. 9: illustrates an example output summary of a generated surgery plan.

FIG. 10: illustrates an example output depicting an IOL selection.

FIG. 11: illustrates an example method for generating an eye surgery plan.

FIG. 12: illustrates an example computer system.

Various eye conditions may involve a refractive error. For example, myopia (nearsightedness) is a condition where a person can see well up close, but has problems seeing far off. Conversely, hyperopia (farsightedness) is a condition where a person cannot see well at near or distance without correction. Both of these conditions are due to an abnormally shaped eye that causes a refractive error and prevents light from properly focusing on the retina. Both of these conditions may be treated with eyeglasses. As a normal part of aging, however, a person may develop presbyopia, which is a condition where the lens in the eye gradually loses its flexibility and thus loses its ability to focus, particularly on objects up close. Astigmatism is another condition where the eye has difficulty producing a single focus point on the retina, and instead produces multiple focus points, either in front of the retina or behind it (or both). Astigmatism usually causes vision to be blurred or distorted, in varying degrees, at all distances. As a person ages, other conditions may arise that require eye surgery, and thereby provide an opportunity to correct some refractive error by eye surgery, which may include lens replacement and/or refractive surgery, like laser-assisted in situ keratomileusis (LASIK).

For example, a person tends to develop cataracts with age. A cataract is a cloudy or opaque area that develops within the lens of the eye. The lens is located inside the eye behind the iris, and is typically clear. The lens is used to focus light onto the retina for clear vision, but a cataract can cause light to scatter and thereby limit the ability of the lens to focus properly. This can lead to vision blur, glare, and dulling of color, which cannot be corrected with glasses or contact lenses. Treatment is typically cataract surgery to replace the cataract-afflicted natural lens with an artificial, intraocular lens (IOL). Additionally, intraocular lenses can also be used to help correct for presbyopia or astigmatism. For example, a toric intraocular lens is designed to differentially focus light in different meridians to correct for astigmatism.

Planning a modern cataract surgery is therefore very complex, particularly since the advent of presbyopia-correcting and astigmatism-correcting (toric) intraocular lenses, which in addition to addressing cataracts, require planning for additional vision correction (e.g., correcting for refraction-error-related conditions). The use of these premium intraocular lenses requires additional steps in the planning process to optimize a patient's outcome. Doctors must carefully assess an enormous amount of patient data, including the patient's desires and expectations, to determine if the patient is even a candidate for one of these premium lenses. The relevant patient data typically resides in an electronic medical record (EMR) system, which maintains a patient's medical history in electronic/digital form. A further complication is that EMR data may be accessible at a doctor's clinic, but the surgery room (OR) is typically in a surgery center or hospital distant from the clinic and typically does not have access to the clinic's EMR system. Therefore, a surgeon cannot view/review EMR records to make changes to a surgery plan or check a patient's relevant medical history if a complication in the OR should arise. If a surgeon were to overlook a subtle problem with the patient's eye, or miss the fact that a data element (e.g., field or entry) in the patient's record had been entered incorrectly, the patient could end up with a poor outcome.

Premium intraocular lenses may not be fully covered by medical insurance and may require an "out-of-pocket" payment to be paid by the patient. A patient paying for a premium lens may have heightened expectations and may be dissatisfied if the final refractive outcome is off target after surgery, or if the surgery has left the patient with residual astigmatism that obligates the patient to wear glasses for optimum vision. In order to evaluate residual astigmatism prior to surgery, the surgeon may visit a website that supports an on-line toric calculator, manually enter a series of data elements, and then transfer that result back to the patient's medical record (e.g., EMR).

In embodiments, a method, device, or system is provided to aid surgical planning. The embodiments generate a surgery plan that would heretofore have required a significant amount of time for an experienced surgeon to achieve, particularly when applied to cataract surgery that may use a premium lens, as explained above.

FIG. 1A illustrates an overview of a surgical planning system in accord with the present invention. A computing system, or device, 11 may extract information from various sources. Computing system 11 may be comprised of one or more devices implementing the present system. Optionally, computing device 11 may be a hand-held device, incorporated into diagnostic equipment, or embodied within a computer-readable non-transitory storage media. In some embodiments, computing device 11 may incorporate a web-based application, and may interface with one or more electronic medical record (EMR) systems 13, either directly or over a computer network. For example, the web-based application may access the patients EMR data from EMR 13 over the Internet 15, and automatically extract relevant clinical information (e.g., patient history data) from the patient's EMR to eliminate the need for manual data entry during cataract surgery planning.

As is explained above, various IOL calculators may be needed to select a specific IOL power for a surgical procedure. Preferably, computing device 11 incorporates multiple well-established IOL calculators. IOL calculators that may not be available within computing device 11 may still be accessible over the Internet 15. For example, the web-based application may access any of IOL Calculator_1 through IOL Calculator_t over the Internet 15, and thereby facilitate cataract surgical planning.

Computing device 11 may also interface with a biometry unit (or diagnostic device) 17, such as an IOLMaster series machines from ZEISS, Jena, Germany. Biometry unit 17 may take various physical measurements and images of a patient's eye. Computing device 11 may have direct access to biometry unit 17, as illustrated by solid arrow 19, or may access biometry unit 17 over the Internet 15, as illustrated by dotted arrow 21. For example, solid arrow 19 may represent a direct wired or wireless connection, such as a wired connection over a local area network, Wi-Fi access to the local area network, a Bluetooth connection, or a USB interface. Again, computing device 11 may extract relevant diagnostic information from biometry unit 17 to eliminate the need for manual data entry during cataract surgery planning.

Alternatively, diagnostic data may be maintained in a biometry data store (diagnostic data store) 18, which may be an integral (e.g., internal) part of Biometry unit 17 or may be an independent unit, such as the FORUM unit from ZEISS, Jena, Germany. For example, biometry unit 17 may transfer diagnostic data to biometry data store 18, which may be accessible over a network, either directly by incorporating a server function, or via a network server. That is, biometry data store 18 may maintain and provide diagnostic data as a cloud (e.g., Internet-accessible) service. Therefore, computing device 11 may access (e.g. obtain, download, extract, etc.) patient diagnostic data directly from biometry data store 18, as illustrated by dotted line 20, if for example, biometry data store 18 is accessible via a local area network. Alternatively, computing device 11 may access patient diagnostic data from biometry data store 18 as a cloud service (e.g. over the Internet), as illustrated by solid line 22.

FIG. 1B illustrates an overview of an alternate embodiment wherein the surgical planning system of FIG. 1A is implemented as a cloud-based system, or application accessible via a web browser. All elements similar to those of FIG. 1A have similar reference characters and are described above. In the present case, much of the functionality of computing device 11 of FIG. 1A is provided by a cloud-based surgery planning system (e.g., server) 11'. That is, cloud-based surgery planning system 11' uses the Internet 15 to communicate with IOL Calculator_1 through IOL Calcuator_t, EMR 13, biometry unit 17, and biometry data unit store 18, and provides services to clients (e.g., doctor 23 and patient 25) via one or more client systems (or devices) 26. Client system 26 may be any web-enabled device (e.g., mobile phone, PDA, tablet computer, desktop computer, notebook, etc.) that supports a web browser 28. Thus, client system 26 may be one or more devices accessible by multiple users. Like in the case of FIG. 1A, doctor 23 may still customize the GUI viewed by patient 25, irrespective of whether patient 25 accesses cloud-based surgery planning system 11' using a different client system 26 than that used by doctor 23.

The present discussions, descriptions, and examples may be applied to the systems of FIGS. 1A and 1B, and any reference to computing device 11 and cloud-based surgery planning system 11' are interchangeable, unless otherwise specified.

Computing device 11 may cross-check medical data entries from its multiple sources and search for consistencies or irregularities. Computer device 11 may issue an alert if symptoms reported by EMR 13 are not corroborated by physical test measurements. For example, if a patient complains of having difficulty seeing objects far off, but physical measurements don't support this condition, then an alert may be issued to identify a possible error. Similarly, if a physical attribute can be identified from both EMR 13 and biometry unit 17 data, then digital computer 11 may compare the values from both sources for consistency. For example, computing device 11 may issue an alert if the axis of refraction, as determined from EMR 13, and the observed axis of selected K-reading (e.g., keratometry readings) differ by more than a predefined degree, e.g., ten degrees. Computing device 11 may further issue an alert when it determines that collected data may not be reliable. For example, a doctor may check an amplification value to determine if a captured image is a good view, but may neglect to check the signal-to-noise ratio (SNR) of the captured image, or other data. If the SNR is low, e.g., below a predefined threshold, then the provided data may not be valid, or reliable. Computer device 11 may issue an alert to notify the doctor that the readings may be erroneous and should not be trusted. In the present system, the doctor may specify through a configuration system (e.g., via questionnaire 27) what checks for consistency or irregularity the surgery planning system 11 should look for, and provide the thresholds that specify when an alert should be issued, or the doctor notified.

Computer device 11 may also review refraction data (e.g., degree to which a lens can focus (converges or diverges) light), keratometries (e.g., measurement of the curvature of the anterior surface of the cornea), and biometry data (diagnostic eye measurements, e.g., axial length, anterior chamber depth, and lens thickness) to check if all are accurate and appropriate (within predefined thresholds) for a given surgery plan. Computing device 11 may also search a patient's medical record (e.g., from EMR 13) to ensure the patient has no co-morbidities that might be a contraindication (a condition or factor that serves as a reason to withhold a certain medical treatment, e.g., drug, procedure, or surgery) for a proposed surgical plan. If any inconstancy is found, computing device 11 may issue an alert to a doctor 23.

EMR data may further be used to generate a surgery plan. For example, if a patient will be having cataract surgery on the right eye, and the patient's medical record indicates that the patient previously had cataract surgery on the left eye, then the present surgery planning system may elect to limit itself to recommending an IOL by the same manufacturer that provided the IOL for the left eye. As a second example, if the EMR data indicates that a patient has an allergy to a specific substance, then the present surgery planning system may eliminate from consideration any medications or procedures that contain or use that substance. If the EMR indicates that cataract surgery is planned on a patient's dominant eye, then this may affect a recommendation of post-operative refractive target for that eye.

In some embodiments, computing device 11 further provides an electronic, or digital, questionnaire to the doctor 23 and/or to a patient 25, as illustrated by arrows 27 and 29, respectively. The doctor 23 may use the questionnaire to submit his or her preferences for various surgical planning options, such as surgical procedures, preferred IOL types, post-op treatment, etc. The doctor 23 may further identify what types of checks (as explained above) should be used to identify possible inconsistencies in the data provided by EMR 13, biometry unit 17, biometry data store 18, and/or patient questionnaire 29. In some embodiments, different doctor preference options may be more heavily correlated to certain patient questions in the patient questionnaire 29, and the patient's questionnaire may be configured in accordance with the doctor's preferences. For example, patient questions that may be more heavily correlated to a particular category option that the doctor has already selected may be eliminated from the patient questionnaire. Computing device 11 may provide a configurable graphical user interface (GUI) 31, which the doctor 23 may configure, or customize, for patient 25, such as to focus on select category options or to provide visual aids to assist the patient, as is explained more fully below. In this case, the submitted doctor preferences may be part of an initialization (configuration) process applicable to all patients, and need not be repeated unless a change in preference is desired. However, on occasion, the present surgical planning system may query the doctor to specify the severity of a patient's specific condition, if it is deemed to be a factor in automated surgery planning.

These preferences may further be used in the automated generation of a surgery plan. For example, the doctor may specify what types of IOLs are not preferred, and the planning system may therefore eliminate those from consideration. Alternatively, the preferences may specify specific IOL models that the doctor prefers (or has access to), and the planning system may use this information when determining an IOL type and model to recommend, as explained below.

Computing device 11 may use data from EMR 13, data digitally extracted from one or more interfaced biometry units 17 and/or biometry data stores 18, doctor's (configuration) preferences extracted from electronic doctor questionnaire 27, and patient's answers extracted from patient questionnaire 29 to automatically create an intelligent, sophisticated patient-specific and eye-specific (e.g., cataract) surgery plan that may include a specific IOL model and power that will work best to meet the patient's visual objectives. That is, digital device 11 suggests which IOL type (or model) and which post-op refractive target (e.g. refractive target, such as near, intermediate, or far) would best meet the patient's needs, and may present these recommendations to the doctor 23. Alternatively, digital device 11 may provide a prioritized list of the top IOL types (or models) and/or post-op targets to the doctor 23. Digital device 11 may then automatically calculate the proper IOL power and astigmatism management options. Digital device 11 may use state-of-the-art toric calculators and arcuate incision nomograms to make recommendations with respect to astigmatism management, e.g., toric IOLs and arcuate incisions. Digital device 11 may execute system data validation to validate the imported data and generate alerts when it detects potential problems with the data.

In addition, digital device 11 may use the collected data to determine whether a patient's eye is eligible for cataract surgery. This may include ensuring documentation of the patient's visual complaints and ensuring that those complaints match the visual acuity or glare disability documented in the patient's medical record (e.g., EMR). Failure to properly document eligibility pre-operatively might expose a surgeon to risk in the form of allegations of Medicare fraud.

Since the above services may be delivered through a web-based, intuitive interface that gives the doctor (or surgeon) access to the surgical plan from any device with an internet connection and a web browser, a surgeon is free to make last-minute checks or changes from a hospital (outpatient) surgical/operating room, which would typically not have access to a clinic's EMR system. Additionally, the surgeon does not have to directly interface with the biometry device 17 to review or edit the surgical plan once the biometry data has been imported into digital device 11.

FIG. 2 illustrates an approach to accessing multiple different EMRs, such as via the Internet. Each EMR (e.g., EMR_1 through EMR_i) may be from a different provider, and thus may require a different communication interface protocol. Digital device 11 may include a collection, or table 35 of different application programming interfaces (APIs) from which to choose. Each API may be mapped to a specific EMR. For example, access to EMR_1 may require use of API_1, access to EMR_2 may require use of API_2, and so on. Optionally, after identifying a specific EMR which digital device 11 wishes to access, digital device 11 may access the corresponding API from the API SELECT table.

FIG. 3 illustrates a grid structure that may be used to score surgical plan options relative to patient answers. The present example shows m patient questions (Patient_Question_1 to Patient_Question_m), and each question has multiple answer options. For example, Patient_Question_1 has three possible answers (Answer Q1_1 to Answer Q1_3), from which the patient may choose. Similarly, Patient_Question_m has v possible answers (Answer_Qm_1 to Answer_Qm_3). The present example also shows multiple surgery planning options, or categories, (Option_1 to Option_n), and each option (or category) has a plurality of electives (or choices). For example, Option_1 has three electives. Each possible patient-question answer may be mapped with a weight (patient-datum weight) to each possible option elective. For example, Answer Q1_1 has a weight of Elective_Op1_Wt1 mapped to the first elective of Option_1; Answer Q1_1 has a (optionally different) weight of Elective_Op2_Wt1 mapped to the first elective of Option_2; Answer_Qm_v has a weight of Elective_Opn_Wtv mapped to the $v^{th}$ elective of Option_n; and so on.

The options (Option_1 to Option_n) and their electives may identify different surgery planning options. For example, Option_1 may refer to a post-op refractive target, and its possible electives may be "Distance", "Intermediate", and "Near". Another option may be IOL-based Treatment method, and its electives may be "Monovision" (where the left and right eye receive IOL lenses of different, but fixed, focal points), "Prebyopic IOL" (where IOUs capable of variable focal points are used) and "Monofocal" (where the left and right eye receive IOL lenses of the same, fixed focal point). Another option may be Procedure, and its electives may be "LRI", Femtosecond (FLAGS), and "Post-op LASIK/PRK). Another option may be Eligibility, and its electives may be, for example, criteria used to determine cataract surgery eligibility, such as "Distance Vision impaired", "Near Vision Impaired", or "Impaired by Glare". Still another option may be IOL Type, and its electives may include a plurality of available IOL types, such as Monofocal IOL, Toric IOL, Multifocal IOL, Multifocal Toric IOL, EDOF IOL, EDOF Toric, etc.

A similar approach may be applied to diagnostic data retrieved from biometry unit 17 and/or biometry data store 18. For example, select diagnostic data may be mapped to specific option elections, and mapped diagnostic data may be assigned weights (diagnostic-datum weights) that may be used in selecting or prioritizing option elections in a manner similar to that described above in with respect to patient data. For example, if diagnostic data indicates that a patient's cornea is thin (within predefined threshold ranges), the present surgery planning system may determine that arcuate incisions (LRI) should not be used, and then determine an expected remaining astigmatism after surgery. In this case, certain thickness threshold ranges may be assigned different weights that affect the confidence level of recommending arcuate incision. A thin cornea thickness below a specific threshold (e.g., a doctor-specified threshold) may be assigned a very low weight (e.g., a negative value) to ensure that arcuate incision is not recommended. Thus, a (select) datum type may be mapped to a category and its electives, and each mapped datum may be given a weight according to its relevance to a specific option and elective. Making a recommendation may include summing the weights (e.g., from the retrieved patient questionnaire and diagnostic data) that are mapped to electives of a category, and identifying the elective with the highest sum within the category. Recommendations and prioritizations may be made by identifying the options and electives with the highest summed scores (e.g., weights).

In summary, digital device 11 may access and process information from four different sources to provide a recommendation. As explained above, the digital device 11 may interface with various ophthalmology EMR systems (e.g., EMR_1 to EMR_i) through one or more API(s) (e.g., API_1 to APIA to import data elements identified (e.g., flagged) as necessary for cataract surgery planning. These data elements typically reside in the EMR, and are typically inputted as a clinician enters (records) data, such as during the course of patient visits. Imported EMR data elements may include:
 a. Patient demographics
 b. Eye problems (e.g. International Classification of Diseases, Tenth Revision, (ICD-10) diagnosis and/or procedure codes)
 c. Medical problems (e.g., ICD-10 codes)
 d. Prior eye surgery (e.g., CPT codes)
 e. Medications
 f. Allergies
 g. Refraction and glasses readings
 h. Visual acuity
 i. Keratometry readings
 j. Pachymetry (corneal thickness)

Similarly, digital device 11 may interface with various diagnostic devices (e.g., biometry unit 17) or diagnostic data storage solutions (e.g., biometry data store 18) that generate/provide data useful in cataract surgery planning. This may include discrete data as well as images generated by these devices/units (e.g., corneal topography, Optical coherence tomography (OCT), etc.). That is, digital device 11 may import discrete data from digital (optical) biometry devices, such as the IOLMaster series and Haag-Streit Lenstar. Imported biometry/diagnostic data elements may include:
 a. Axial length
 b. Keratometry readings
 c. Anterior chamber depth (ACD)
 d. Lens thickness
 e. White-to-white (e.g., corneal diameter as determined by the horizontal white-to-white direction)

The digital device 11's doctor's questionnaire may obtain configuration settings during an initial configuration process so that the doctor's questionnaire need only be filled out once for all patients. For example, during the initial implementation process, the doctor 23 (e.g., cataract surgeon) answers a series of questions that provide digital device 11 (and its application) with the doctor's preferences in areas where surgeons may differ in their approach to cataract surgery. These configurations allow the application to deliver recommendations tailored to each individual surgeon. Some of the configurations, as applied to IOL recommendations, may include:
 a. Arcuate incision nomogram adjustments (WTR (e.g., with-the-rule) and ATR (against-the-rule))
 b. Incision size and location
 c. Preferred targets for each IOL category
 d. Data validation parameters (axial length, variability in refraction and keratometry axes and cylinder powers, etc.)
 e. IOL models available to surgeon
 f. IOL model SRK-T A-constant (defaults are ULIB constants)
 g. Criteria considered relative contraindications for each IOL category
 h. Surgically induced astigmatism (SIA)
 i. Cataract surgery co-morbidity concerns (diagnoses and prior surgeries)

As stated above, digital device 11 may provide a digital patient questionnaire 29 (configurable by the surgeon 23) that extracts answers from the patient that gives the doctor and the present surgery planning system insight into the patient's desires and expectations. In certain situations, the application may also ask the doctor to answer a few questions that it cannot derive without specific physician input. These may generally relate to the severity of associated diagnoses (corneal problems, macular problems, etc.) that could affect an IOL recommendation. Example of patient questions may include:
 a. Would you prefer to be less dependent on glasses?
 b. After cataract surgery would you mind wearing reading glasses?
 c. Are you willing to trade some quality of vision to be less dependent on glasses?
 d. Which is most important to you: mid-range or near vision?
 e. Would you prefer to be less dependent on glasses at distance only, or distance and near?
 f. Have you enjoyed wearing monovision contacts in the past?

Digital device 11 may also use the patient's answers to determine if an eye is eligible for eye surgery. The digital device 11 may look at the documented patient complaints (distance vision, near vision, and glare), reviews the eye's visual function (visual acuity, glare testing), optionally check insurance provider criteria (such as provided by Medicare, the U.S. federal health insurance program), and then determines if the eye is eligible.

Digital device 11 processes all of the imported and configured information through a grid function (e.g., as illustrated in FIG. 3 as applied to the patient questionnaire) that assigns a weighting (weight) to IOL types (e.g., monofocal IOL, monofocal toric IOL, multifocal IOL, multifocal toric IOL, EDOF IOL, EDOF toric IOL, accommodative IOL, accommodative toric IOL, NC IOL) and to post-operative refractive targets (e.g., distance, intermediate, near). The application summates the information (e.g., weights) to create a ranking for each IOL category and post-operative refractive target (sometimes termed "Target"). The category with the highest score becomes the recommended category. The target (distance, intermediate, or near) with the highest score becomes the recommended target. The application (e.g., digital device 11) also determines whether a monovision system might be preferable to a presbyopic IOL if the patient desires to be spectacle free after surgery. Once the application knows which IOL category would be best for the patient, it processes the information through a second grid function to determine which IOL model in that category would be best. The application may differentiate the IOL models (e.g. in the second grid function) within a category by surgeon preferences, lens material, power availability, and sphericity.

As stated above, digital device 11 may access multiple different (IOL) calculators, (both natively and remotely). For example, digital device 11 may include the Barrett Universal II formula for power calculations. This formula may run natively in the application. The doctor may also choose to use the Holladay II formula, which digital device 11 may access by sending and receiving data (e.g., over the internet) through an API to a proprietary web-hosted calculator. Lenstar IOL users may choose to import IOL power recommendations from the Hill RBF formula. A doctor/surgeon may determine which of these formula results to use for each procedure (for example, this may be part of the initialization preferences). This process yields the IOL power and predicted residual spherical equivalent.

Digital device 11 may include the Barrett Toric calculator and the Abulafia-Koch toric calculator, both of which may run natively in the application. These calculators may process every cataract surgery procedure to determine the predicted residual refractive error, and what toric IOL power would be recommended. Both calculators include state-of-the-art posterior corneal astigmatism adjustments.

Digital device 11 may include the most commonly used arcuate incision nomograms, e.g. Nichamin and Donnenfeld. If an eye requires astigmatism management and a toric lens is either inadequate or not recommended, the application will automatically determine the length, axis, optical zone, and depth of the arcuate incisions, and the predicted post-op refraction.

The same grid function that provides a ranking for each IOL category may also generate alerts if the selected IOL is associated with any potential problems. The systematic data validation process may also generate alerts. For example, the application may notify the surgeon that the axis of the refraction and the axis of the selected K-reading differ by more than 10 degrees. This could be an indication of a data entry problem, or measurement error. The application may ask the user (doctor) to acknowledge these alerts prior to final approval of the surgical plan.

Surgery plan outputs of digital device 11 may include:
1. Cataract surgery eligibility
2. IOL model
3. IOL power
4. Toric power and axis (if IOL is a toric lens)
5. Arcuate incision parameters
6. Alerts In some embodiments, the function(s) of digital device 11 may be embodied in a web-based server and/or client-server, such as a stand-alone web-based application or cloud service, or embodied as an application within an EMR system (either web-based server or client-server based), or as an extension of a specific data storage system like ZEISS FORUM. It could also reside in a specific device such as a biometry unit. The digital device 11 (or client system 26) may be implemented as multiple devices. For example, the doctor 23 may use a desktop computer as digital device 11 to access the present surgery planning system, and the patient 25 may use a tablet computer or mobile phone application to access the present surgery planning system.

The IOL recommendations and the cataract surgery eligibility assessment may be independent functions and could be implemented independently. The present invention may be embodied in a mobile device (e.g., mobile phone) or embodied as a mobile application.

FIG. 4 illustrates an example embodiment of digital device 11, which may be a mobile device (or optionally be a mobile application within the mobile device). In the present example, digital device 11 includes a display (or screen) 41 and camera 43. Display 41 may be a touch sensitive screen for interfacing with a user such as a patient or doctor. Mobile device 11 may provide other means of interfacing with a user, such as mouse, keyboard, or other known input mechanism. Display 41 is shown displaying a patient questionnaire, as customized, for example, by doctor input(s). In the present example, doctor customization results in a questionnaire that excludes questions that are more heavily directed to options 2 through 4, but shows questions directed to options (categories) 1 and 5. That is, questions 45 are more heavily directed toward option 1 (and its electives), and questions 47 are more heavily directed toward option 5 (and its electives). Alternatively, digital device 11 may incorporate learning mechanisms for personalizing the questionnaire and adapting to the most relevant questions for each user. For example, non-relevant questions may be excluded. Further alternatively, a user (doctor or patient) may be permitted to add questions. If a user adds a question, this question may be offered to other users. In this case, the learning mechanisms identify added questions that could be of value for every user, to determine which questions should be added or excluded for other users. Further alternatively, an initial default configuration may be offered, and digital device 11 may customize itself to the user, as the user submits answers (such as by using the learning mechanism). Digital device 11 may also learn the most effective configurations, over time, and provide those configurations to other users, including ratings.

Display 41 may further provide a simulated image 49 that may simulate different vision (impairment) conditions to inform the patient of what may be expected after surgery, or to provide a reference for the patient to understand certain vision conditions described in the questionnaire. For example, the questionnaire may ask the patient to input his/her degree of glare. This question is subjective, and simulated image 49 may be used to illustrate different degrees of glare, or other vision condition, by use of a slider 50 (or other adjustment mechanism) to control the degree of glare. A patient may indicate when he/she is satisfied with a currently displayed degree, such as by actuating a select input (e.g., tapping on simulated image 49), and device 11 may respond by capturing the current degree (as indicated by the current position of slider 50) as part of the patients answer to a question. The simulated image maybe based on pre-stored image, or may be produced by capturing (video) images from front-facing camera 43 or from a rear-facing camera, not shown.

In this manner, the patient may obtain a more immediate understanding of how different viewing conditions may affect his/her surroundings.

Digital device 11 may provide input options 51 to select among multiple types of simulated images, such as a near refractive (target) condition, an intermediate refractive (target) condition, far refractive (target) condition, day-light condition, night-time condition, haze, glare, etc.

FIG. 5 illustrates an example of clinical questions posed to a doctor or clinician. The clinical questions allow the doctor to answer specific questions about the severity of eye problems that the present surgery planning system detected by reviewing the imported EMR data. An EMR usually does not provide information on severity, so the present surgery planning system may need to add that information to its analysis by asking the doctor's opinion. For example, mild cornea guttatae may not be a contraindication for a multifocal lens, but moderate or severe guttatae would be a contraindication and thus preclude multifocal lenses from consideration (e.g., from being recommended by the present surgery analysis system).

FIG. 6 illustrates an example summary of a patient questionnaire interface. As shown, multiple questions may be directed to similar categories. For example, questions 2 and 3 are labeled as having been directed to a glare complaint.

FIG. 7 illustrates an example interface to determine eligibility for cataract surgery. As shown, eligibility may be separately directed to each of the right eye and left eye. Patient answers may be displayed in tabular form to better indicate which set of patient answers identify the patient as begin eligible.

FIG. 8 illustrates an example interface displaying alerts. In the present example, two alerts are shown. The doctor must acknowledge that he/she is aware of these alerts before proceeding. This gives the doctor a chance to recheck test results to determine where an error may have arisen.

Figure 1A:
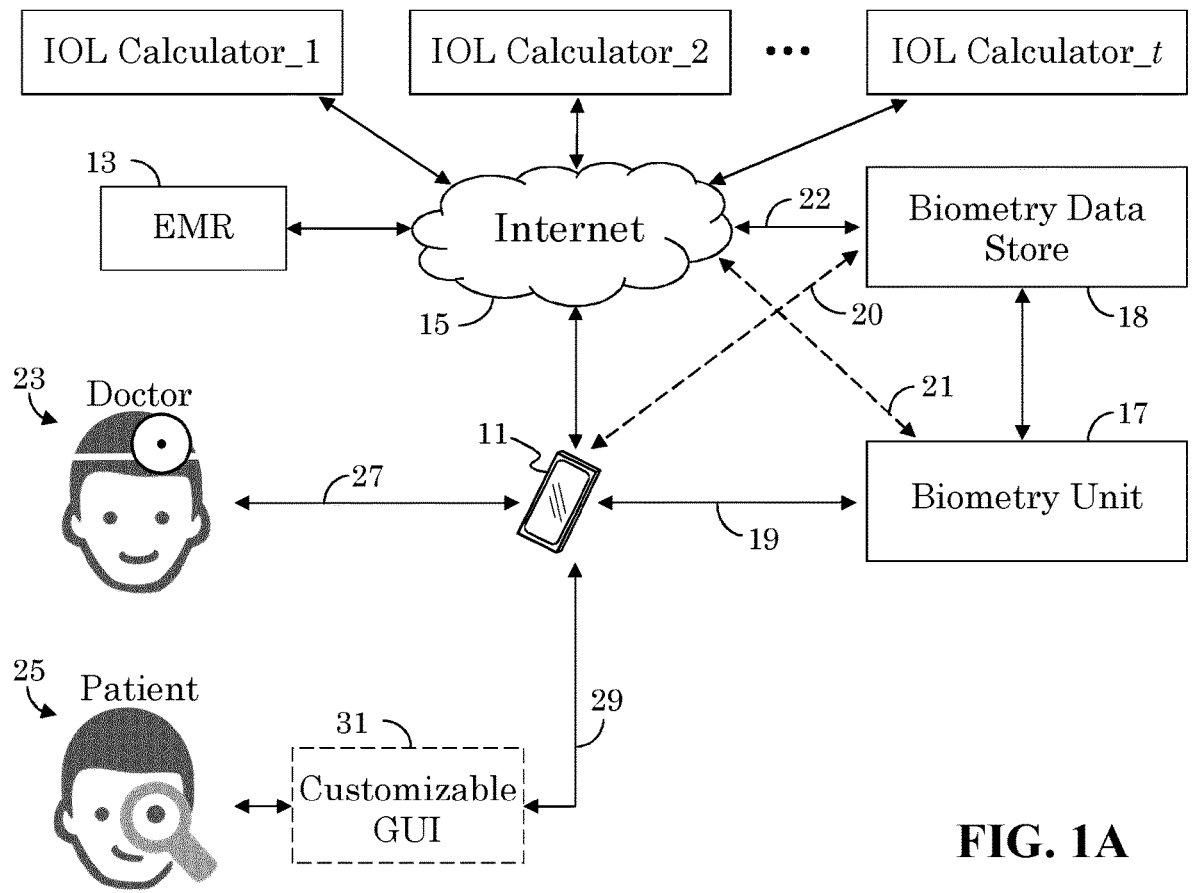
Figure 2:
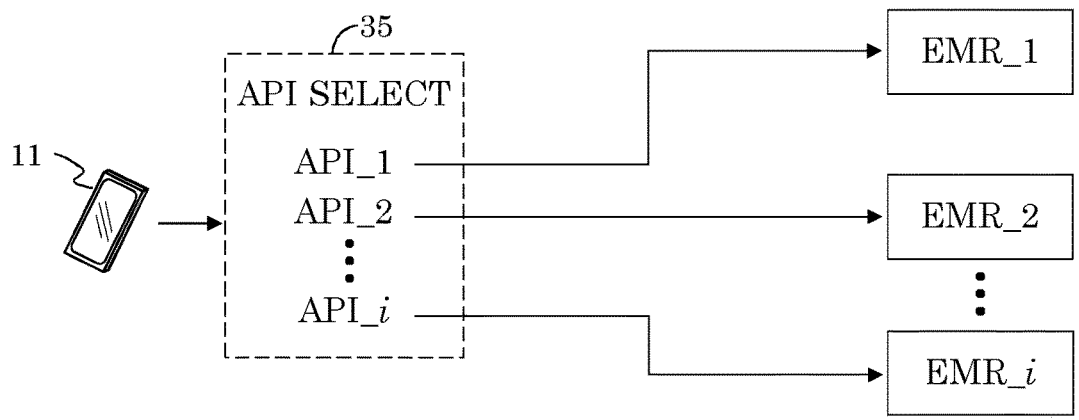
Figure 1B:
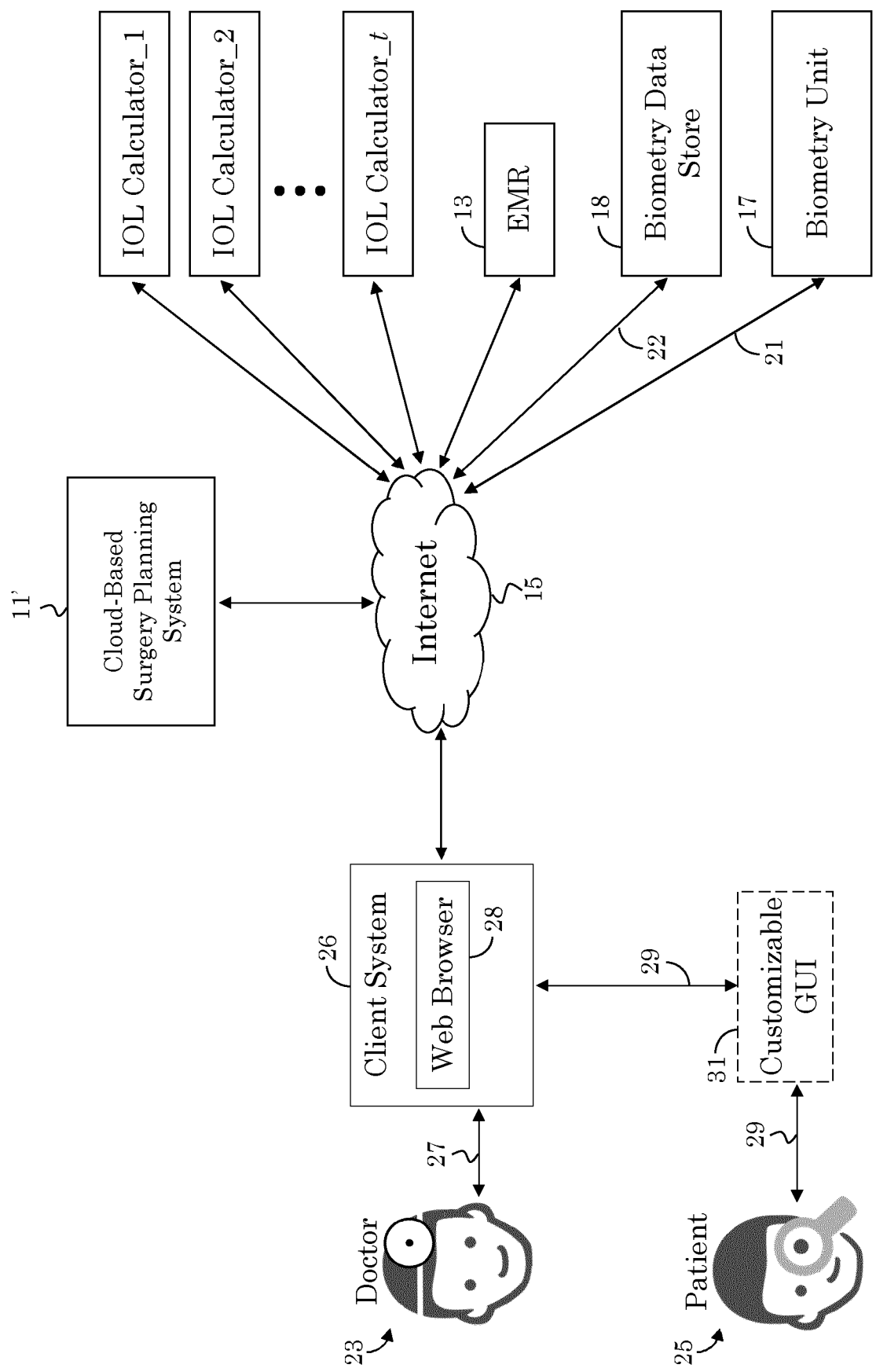
Figure 3:
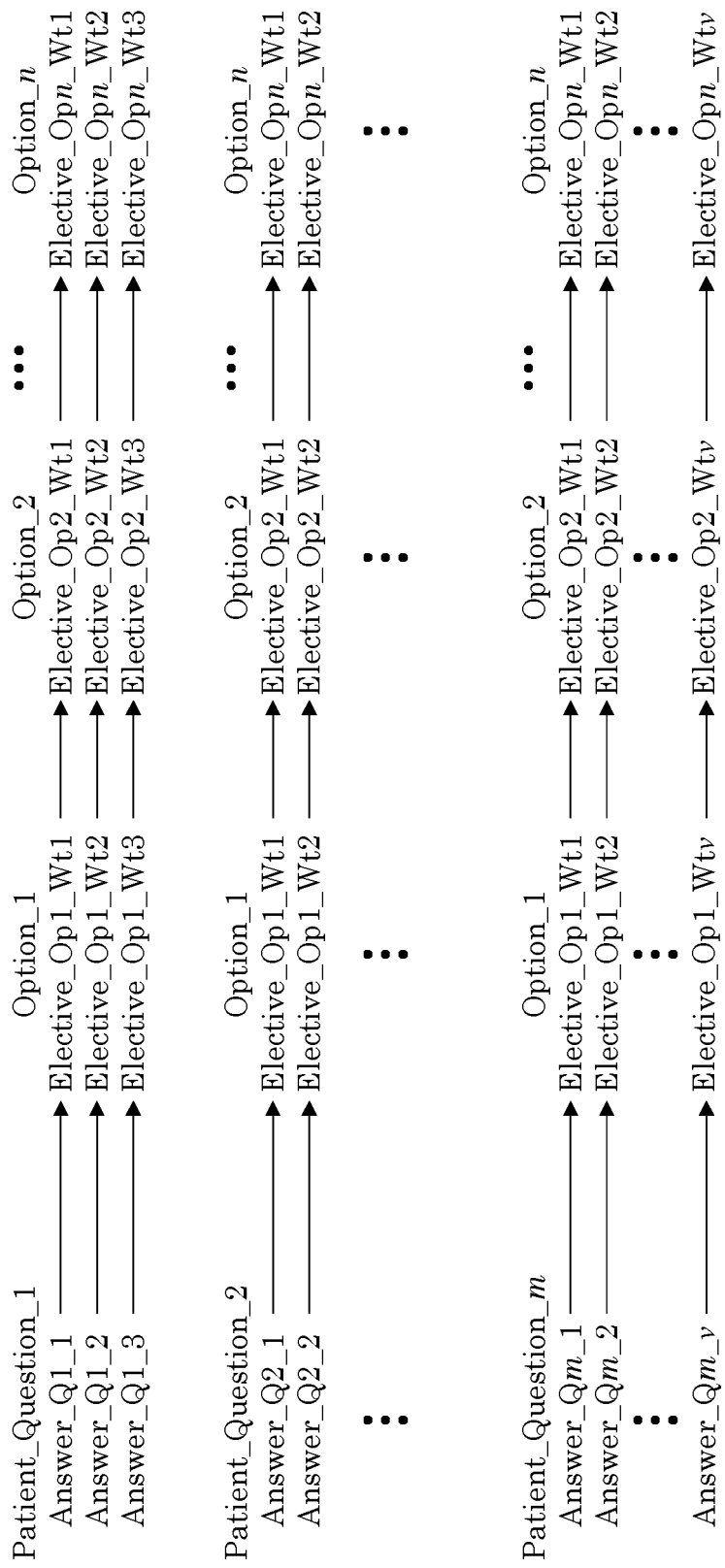
Figure 4:
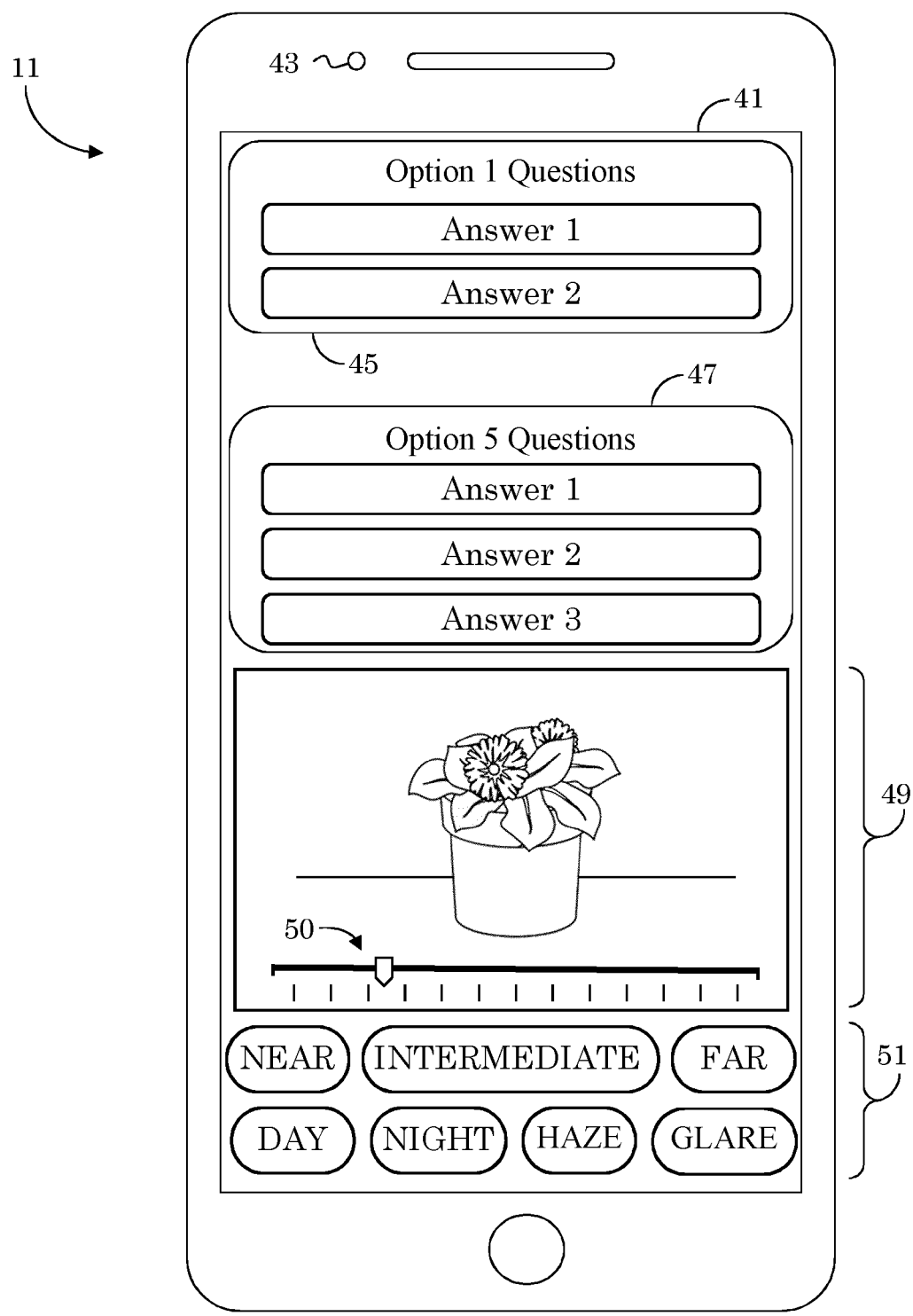
Figure 5:
Figure 8:
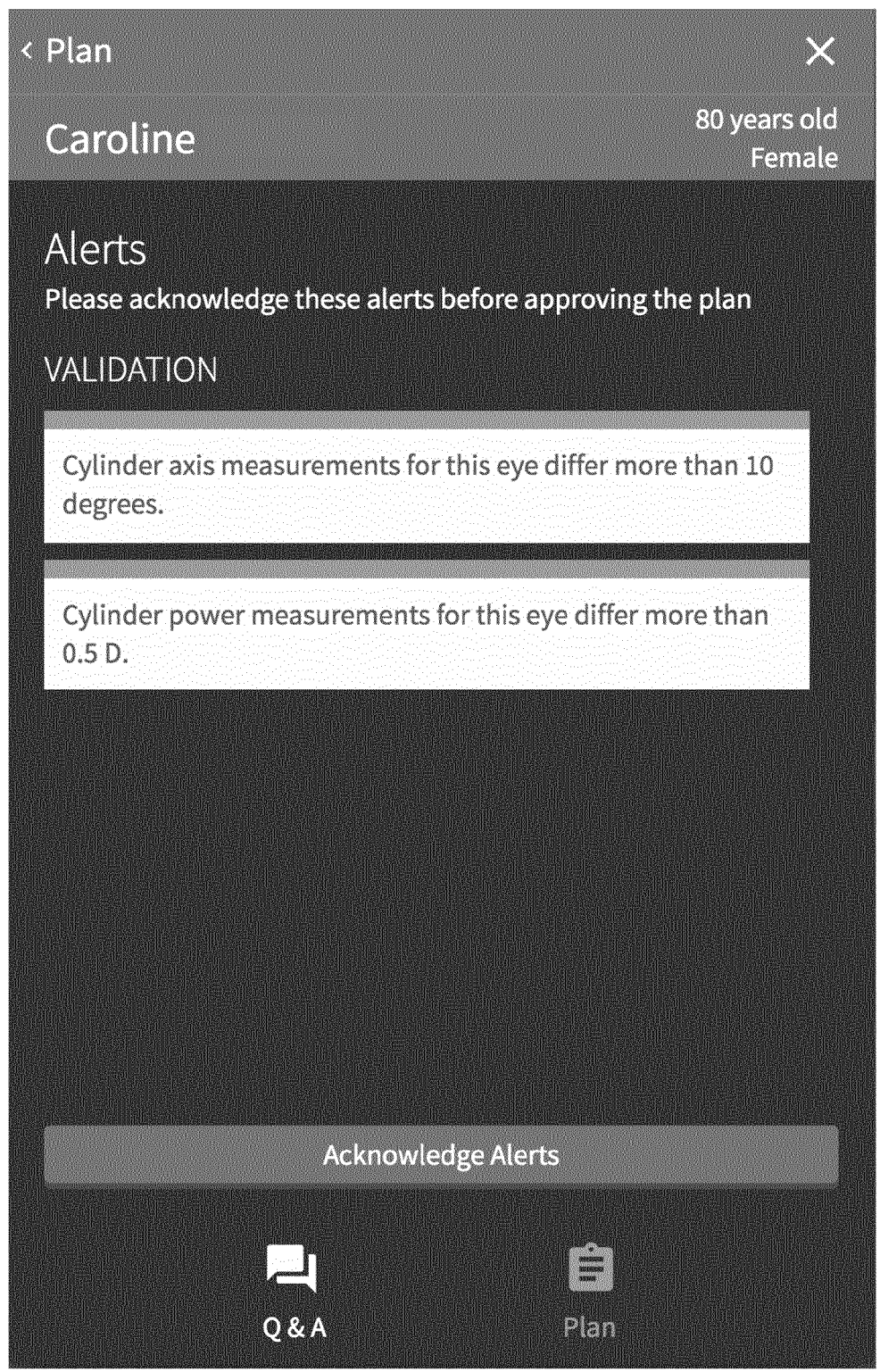
Figure 9:
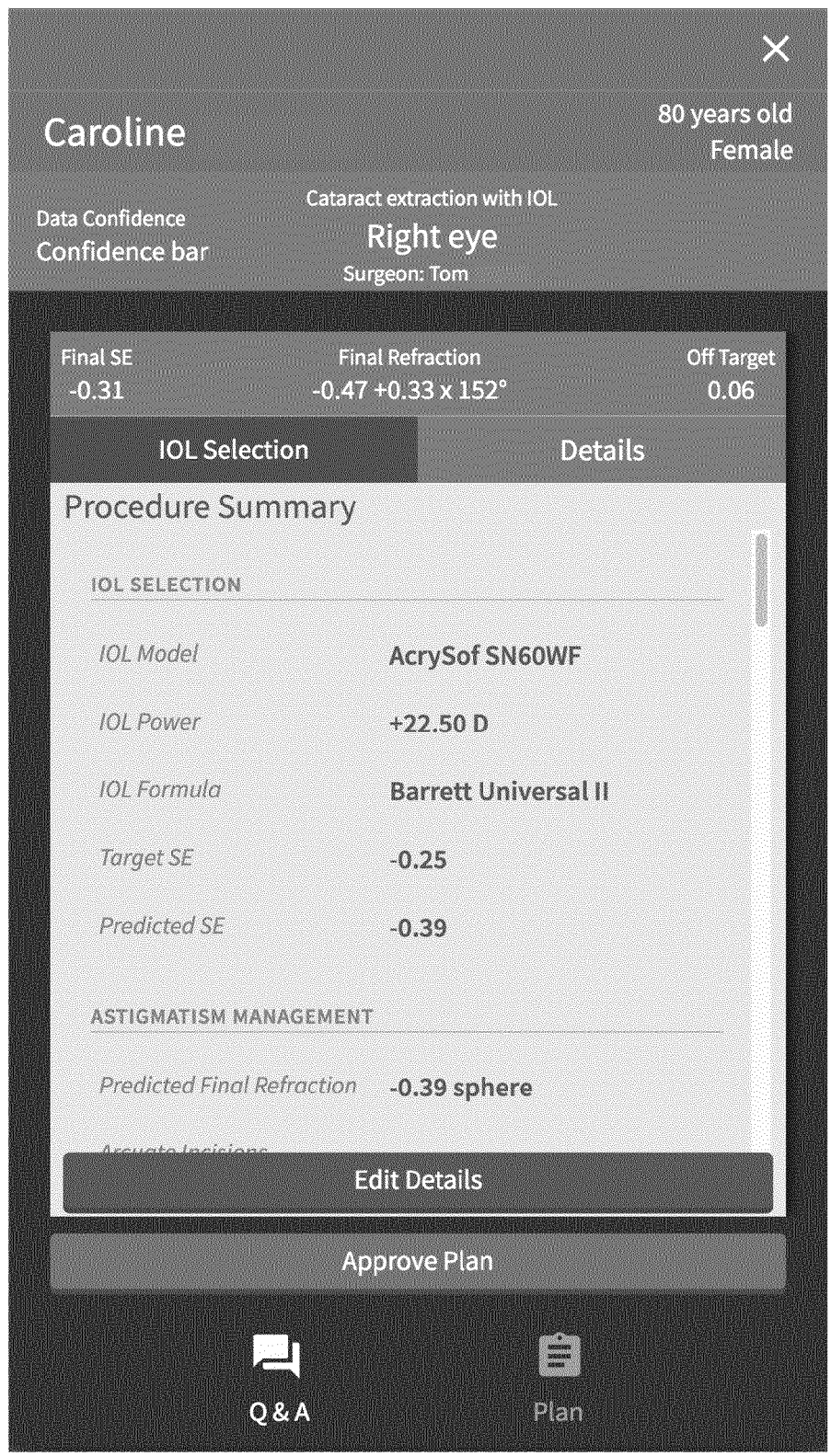
FIG. 9 illustrates an example output summary of a generated surgery plan. The summary may include the recommended IOL model, recommended IOL power, formula (e.g. calculator) used, the (post-operative refractive) target, and predicted refractive target.
Figure 10:
FIG. 10 illustrates an example output depicting an IOL selection summary. Additional surgery planning details are illustrated graphically.
Figure 11:
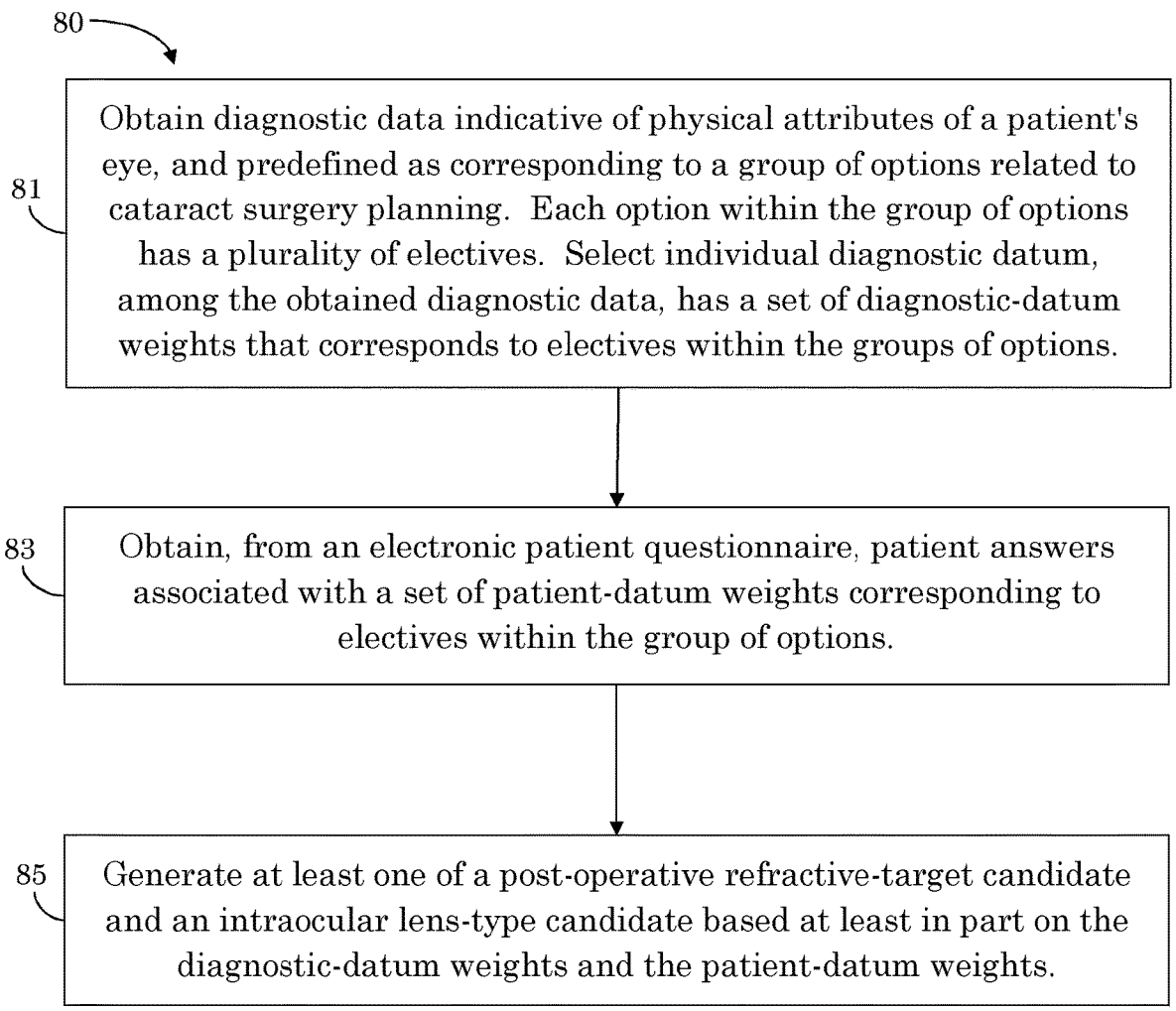

FIG. 11 illustrates an example method 80 for generating an eye surgery plan for a patient. The method may begin at step 81, where diagnostic data indicative of physical attributes of a patient's eye, and predefined as corresponding to a group of options related to cataract surgery planning, is obtained. The diagnostic data may be obtained by electronically interfacing with a biometry unit 17 or a biometry data store 18, either directly or on a computer network, such as the Internet 15. Each option within the group of options has a plurality of electives. Select individual diagnostic datum, among the obtained diagnostic data, has a set of diagnostic-datum weights that corresponds to electives within the groups of options. At step 83, an electronic patient questionnaire is used to obtain patient answers associated with a set of patient-datum weights corresponding to electives within the group of options. At step 85, least one of a post-operative refractive-target candidate and an intraocular lens-type candidate is generated based at least in part on the diagnostic-datum weights and the patient-datum weights. Some embodiments may repeat one or more steps of the method of FIG. 11, where appropriate. Although this disclosure describes and illustrates particular steps of the method of FIG. 11 as occurring in a particular order, this disclosure contemplates any suitable steps of the method of FIG. 11 occurring in any suitable order.

Figure 12:
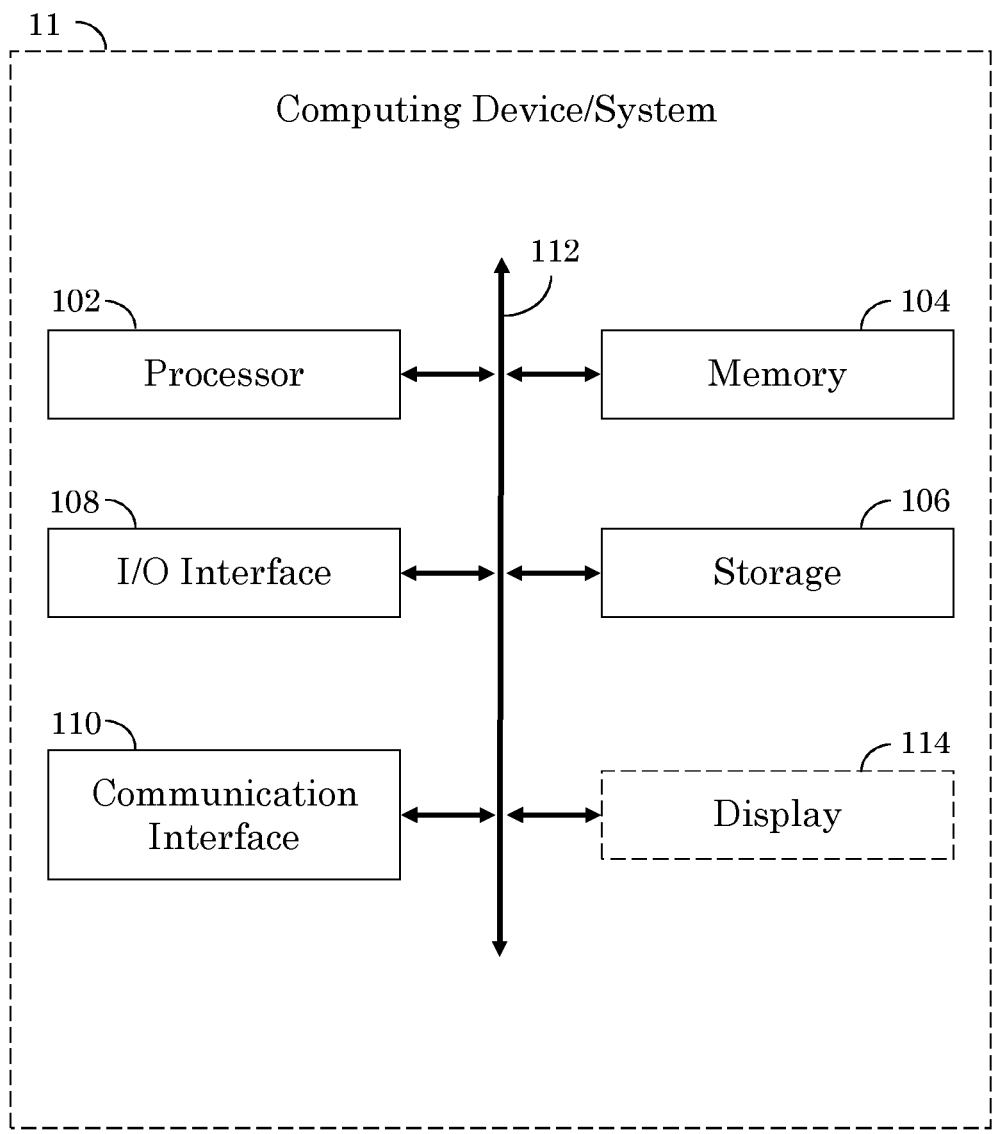

FIG. 12 illustrates an example computer device (or computer system) 11. In some embodiments, one or more computer systems 11 may perform one or more steps of the method of FIG. 11. Computer system 11 may take any suitable physical form. For example, computer system 11 may be an embedded computer system, a system-on-chip (SOC), a single-board computer system (SBC) (such as, for example, a computer-on-module (COM) or system-on-module (SOM)), a desktop computer system, a laptop or notebook computer system, a mesh of computer systems, a mobile telephone, a personal digital assistant (PDA), a server, a tablet computer system, or a combination of two or more of these. Where appropriate, computer system 11 may reside in a cloud, which may include one or more cloud components in one or more networks.

In some embodiments, computer system 11 includes a processor 102, memory 104, storage 106, an input/output (I/O) interface 108, a communication interface 110, and a bus 112. Computer system 11 may optionally also include a display 114, such as a computer monitor or screen. Processor 102 includes hardware for executing instructions, such as those making up a computer program. For example, processor 102 may be a central processing unit (CPU) or a general-purpose computing on graphics processing unit (GPGPU). Memory 104 may include main memory for storing instructions for processor 102 to execute or to hold interim data during processing. For example, memory 104 may include random access memory (RAM), such as dynamic RAM (DRAM) or static RAM (SRAM). In some embodiments, storage 106 may include long-term or mass storage for data or instructions. For example, storage 106 may include a hard disk drive (HDD or SSD), flash memory, ROM, EPROM, or other type of non-volatile memory. I/O interface 108 may include one or more interfaces for communication with I/O devices, which may enable communication with a person (user). Communication interface 110 may provide network interfaces for communication with other systems or networks. For example, communication interface 110 may include a network interface controller (NIC) and/or a wireless NIC for communication with another computer system on a network. Communication interface 110 may further include a Bluetooth interface or other type of packet-based communication. Bus 112 may provide a communication link between the above mentioned components of computing system 11.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

The invention claimed is:

1. A method for generating an eye surgery plan for a patient, the method comprising, by a computing device:
obtaining diagnostic data indicative of physical attributes of the patient's eye predefined as corresponding to a group of options related to cataract surgery planning, each option within the group of options having a plurality of electives, select individual diagnostic datum, among the obtained diagnostic data, having a set of diagnostic-datum weights corresponding to electives within the groups of options, said diagnostic-datum weights being used to select or prioritize option elections;
obtaining, from an electronic patient questionnaire, patient answers associated with a set of patient-datum weights corresponding to electives within the group of options, said patient-datum weights being used to select or prioritize option elections;
generating at least one of a post-operative refractive-target candidate and an intraocular lens-type candidate based at least in part on the sum of the diagnostic-datum weights and the sum of the patient-datum weights of the associated elective;

determining whether the patient is eligible for cataract surgery based at least in part on the patient-datum weights and insurance provider criteria;

submitting the at least one of the post-operative refraction target candidate and intraocular lens (IOL) type candidate to at least one of an intraocular power calculator, a toric intraocular calculator, and an arcuate incision calculator;

identifying, as part of generating an eye surgery plan, at least one of a specific intraocular lens model, a intraocular lens power, toric power and axis, and arcuate incision parameters based at least in part on the configuration settings and the calculation results from the accessed calculator; and outputting the generated eye surgery plan, including: (1) cataract surgery eligibility; (2) intraocular lens model; (3) intraocular lens power; (4) toric power and axis if the intraocular model is a toric lens; (5) arcuate incision parameters; and (6) alert of any inconsistency between the patient answers and the obtained diagnostic data.

2. The method of claim 1, wherein the select individual diagnostic datum is indicative of a physical measurement value, and the individual weights in the associated set of diagnostic-datum weights are based on the associated indicated physical measurement value.

3. The method of claim 1, wherein the diagnostic data is obtained from one of a diagnostic device and a diagnostic data store.

4. The method of claim 1, further comprising:
obtaining, from an electronic doctor questionnaire, doctor's answers to questions addressing doctor-preferences related to at least one option within the group of options, the doctor's answers defining configuration settings;
configuring a graphical user interface based at least in part on the configuration settings, the graphic-user interface embodying said electronic patient questionnaire.

5. The method of claim 1, further comprising:
obtaining, from an electronic medical record (EMR) system, EMR data of the patient predefined as corresponding to at least one option within the group of options related to cataract surgery planning, wherein:
the generating of the at least one of the post-operative refractive-target candidate and the intraocular lens-type candidate, further includes eliminating from consideration at least one elective based on the obtained EMR data.

6. The method of claim 5, further comprising:
determining whether the patient is eligible for cataract surgery based at least in part on the obtained EMR data, patient-datum weights, and insurance provider criteria.

7. The method of claim 5, further comprising:
comparing a physical attribute of the patient's eye as determined from the obtained EMR data and as determined from obtained diagnostic data, and
outputting an alert if they differ by more than a predefined threshold.

8. The method of claim 7, further comprising:
obtaining, from an electronic doctor questionnaire, doctor's answers to questions addressing doctor-preferences related to at least one option within the group of options, the doctor's answers defining configuration settings;
wherein the physical attribute and threshold are predefined by the configuration settings.

9. The method of claim 8, wherein the generated at least one of the post-operative refraction target candidate and intraocular lens (IOL) type candidate is output as a proposal for doctor approval, the method further comprising:
in response to a doctor's endorsement of the outputted proposal, accessing at least one of an intraocular power calculator, a toric intraocular calculator, and an arcuate incision calculator, and identifying a specific intraocular lens model based at least on the configuration settings defined by the doctor's answers and calculation results from the accessed calculator.

10. The method of claim 1, further comprising:
outputting an alert in response to a signal-to-noise ratio of at least part of the diagnostic data being below a predefined threshold.

11. The method of claim 1, wherein:
the electronic patient questionnaire includes a display that simulates a vision condition to a specified degree of severity.

12. The method of claim 1, wherein the options within the group of options includes at least one of a post-operative refraction target option, a treatment method option, an intraocular lens type option, an operation procedure type option, and a surgery eligibility check option.

13. The method of claim 1, wherein:
the group of options includes a post-operative refractive target option; and
electives within the post-operative refractive target option include a distance refractive-range target, an intermediate refractive-range target, and a near refractive-range target.

14. The method of claim 1, wherein:
the group of options includes an intraocular-based-treatment option; and
electives within the intraocular-based-treatment option include a monofocal treatment elective, presbyopic treatment elective, and a monofocal treatment elective.

15. The method of claim 1, wherein:
the group of options includes an operation procedure type option; and
electives within the operation procedure type option include Limbal Relaxing Incisions, Femtosecond Laser-Assisted Cataract Surgery, and post-operative cornea shaping by laser.

16. The method of claim 1, wherein:
the group of options includes an intraocular-type option; and
the electives within the intraocular-type option include at least four of monofocal IOL, toric IOL, multifocal IOL, multifocal toric IOL, EDOF IOL, EDOF toric IOL, accommodative IOL, accommodative toric IOL, and A/C IOL.

17. The method of claim 1, further comprising:
establishing a network connection with a diagnostic data store, and obtaining the diagnostic data via a network;
invoking a web-browser; and
using the web-browser to display the electronic patient questionnaire.

18. One or more computer-readable non-transitory storage media embodying software that is operable when executed to:
obtain diagnostic data indicative of physical attributes of the patient's eye predefined as corresponding to a group of options related to cataract surgery planning, each option within the group of options having a plurality of electives, select individual diagnostic datum, among the obtained diagnostic data, having a set of diagnostic-datum weights corresponding to electives within the groups of options;

obtain, from an electronic patient questionnaire, patient answers associated with a set of patient-datum weights corresponding to electives within the group of options;

generate at least one of a post-operative refractive-target candidate and an intraocular lens-type candidate based at least in part on the sum of the diagnostic-datum weights and the sum of the patient-datum weights of the associated elective;

determine whether the patient is eligible for cataract surgery based at least in part on the patient-datum weights and insurance provider criteria;

submit the at least one of the post-operative refraction target candidate and intraocular lens (IOL) type candidate to at least one of an intraocular power calculator, a toric intraocular calculator, and an arcuate incision calculator;

identify, as part of generating an eye surgery plan, at least one of a specific intraocular lens model, a intraocular lens power, toric power and axis, and arcuate incision parameters based at least in part on the configuration settings and the calculation results from the accessed calculator; and output the generated eye surgery plan, including: (1) cataract surgery eligibility; (2) intraocular lens model; (3) intraocular lens power; (4) toric power and axis if the intraocular model is a toric lens; (5) arcuate incision parameters; and (6) alert of any inconsistency between the patient answers and the obtained diagnostic data.

19. The media of claim 18, further comprising:

obtain, from an electronic medical record (EMR) system, EMR data of the patient predefined as corresponding to at least one option within the group of options related to cataract surgery planning, wherein:

the step to generate at least one of the post-operative refractive-target candidate and the intraocular lens-type candidate, further includes eliminating from consideration at least one elective based on the obtained EMR data.

* * * * *